(12) United States Patent
Lei et al.

(10) Patent No.: US 9,505,719 B2
(45) Date of Patent: Nov. 29, 2016

(54) SYNTHESIS AND USE OF KINASE INHIBITORS

(71) Applicant: VERASTEM, INC., Needham, MA (US)

(72) Inventors: Yixiong Lei, Newark, DE (US); Carl Henry Behrens, Newark, DE (US); Hui-Yin Li, Hockessin, DE (US); Connie L. Sun, Palo Alto, CA (US)

(73) Assignee: VERASTEM, INC., Needham, MA (US)

( * ) Notice: Subject to any disclaimer, the term of this patent is extended or adjusted under 35 U.S.C. 154(b) by 0 days.

(21) Appl. No.: 13/961,517

(22) Filed: Aug. 7, 2013

(65) Prior Publication Data

US 2014/0235635 A1 Aug. 21, 2014

Related U.S. Application Data

(63) Continuation of application No. 13/807,642, filed as application No. PCT/US2011/042169 on Jun. 28, 2011, now abandoned.

(60) Provisional application No. 61/359,942, filed on Jun. 30, 2010.

(51) Int. Cl.
*C07D 213/74* (2006.01)
*C07D 279/10* (2006.01)
*C07D 413/12* (2006.01)

(52) U.S. Cl.
CPC ........... *C07D 213/74* (2013.01); *C07D 279/10* (2013.01); *C07D 413/12* (2013.01)

(58) Field of Classification Search
CPC . C07D 213/74; C07D 279/10; C07D 413/12
See application file for complete search history.

(56) References Cited

U.S. PATENT DOCUMENTS

| 4,656,182 | A | 4/1987 | Horwell |
|---|---|---|---|
| 2004/0006005 | A1 | 1/2004 | Bhanot |
| 2005/0090515 | A1 | 4/2005 | Pease et al. |
| 2008/0119515 | A1 | 5/2008 | Siddiqui et al. |
| 2008/0193518 | A1 | 8/2008 | Zarkadas et al. |
| 2009/0203709 | A1 | 8/2009 | Steinberg et al. |
| 2010/0317663 | A1 | 12/2010 | Adams et al. |

FOREIGN PATENT DOCUMENTS

| CN | 1335838 A | 2/2002 |
|---|---|---|
| CN | 101119976A A | 2/2008 |
| WO | 0039101 A1 | 7/2000 |
| WO | 0230414 A1 | 4/2002 |
| WO | 2004002410 A2 | 1/2004 |
| WO | 2006/053755 A1 | 5/2006 |
| WO | 2006087387 A1 | 8/2006 |
| WO | 2007050574 A1 | 5/2007 |
| WO | 2008/011154 A2 | 1/2008 |
| WO | 2008/115369 A2 | 9/2008 |
| WO | 2009/105498 A1 | 8/2009 |
| WO | 2009153589 A1 | 12/2009 |
| WO | 2011019943 A1 | 2/2011 |
| WO | 2011133668 A2 | 10/2011 |

OTHER PUBLICATIONS

European Search Report for International Application No. PCTUS2011042169 Dated Jun. 23, 2014.
European Search Report related to PCT/US2010045359 dated Dec. 12, 2012.
Guan, "Role of Focal Adhesion Kinase in Integrin Signaling", Int J Biochem Cell Biol., 29(8-9), pp. 1085-1096, (1997).
H Sawai, et al. (2005), "Activation of focal adhesion kinase enhances the adhesion and invasion of pancreatic cancer cells via extracellular signal-regulated kinase-1/2 signaling pathway activation" Molecular Cancer, 4:37.
International Preliminary Report on Patentability for PCT/US2011/42162 dated Jan. 8, 2013.
International Search Report for PCT/US 11/42169, dated Jun. 28, 2011.
International Search Report for PCT/US2011/42162 dated Nov. 4, 2011.
Lietha et al., Crystal Structres of the FAK Finase in Complex with TAE226 and Related Bis-Anilino Pyrimidine inhibitors Reveal a Helical DFG Confromation. PLos ONE, Nov. 2008, vol. 3, Iss 11, pp. 1-11.
Schaller et al, "PND-1186 FAK inhibitor selectively promotes tumor cell apoptosis in three dimensional environments" Cancer Biology & Therapy, vol. 9, No. 10, May 15, 2010, pp. 791-793.
Search Report & Written Opinion for PCT/US2010/045359, mailed Oct. 5, 2010.
Supplementary European Search Report for Application No. EP11804122 dated Oct 31, 2014.
Tanjoni et al. "PND-1186 FAK inhibitor selectively promotes tumor cell apoptosis in three dimensional environments" Cancer Biology & Therapy, vol. 9, No. 10, May 15, 2010, pp. 764-777.
Walsh et al. "Oral delivery of PND-1186 FAK inhibitor decreases tumor growth and spontaneous breast to lunch metastasis in preclinical models", Cancer Biology & Therapy, vol. 9, No. 10, May 15, 2010, pp. 778-790.
Written Opinion for PCT/US 11/42169, dated Jun. 28, 2011.
Written Opinion for PCT/US2011/42162 dated Nov. 4, 2011.

*Primary Examiner* — Rebecca Anderson
(74) *Attorney, Agent, or Firm* — Lando & Anastasi, LLP

(57) ABSTRACT

An improved synthesis of a class of inhibitor of Focal Adhesion Kinase (FAK) is provided, wherein use of an expensive palladium-based catalyst is reduced and reaction yields and product purities are improved. Two key reactions of coupling of aryl halides with anilines are optimized with the surprising discovery that the palladium-based catalyst can be dispensed with entirely in one of the reactions. The invention also provides the use of the FAK-inhibitory compounds in the treatment of inflammatory and immune disorders and of arthritis.

31 Claims, 5 Drawing Sheets

*Scheme 3: Flowchart for SF-1 synthesis process*

Scheme 4: Flowchart for SF-1 hydrochloride process

SYNTHESIS AND USE OF KINASE INHIBITORS

CROSS-REFERENCE TO RELATED APPLICATIONS

This application is a Continuation application of Ser. No. 13/807,642 filed Dec. 28, 2012 as National Stage Application under 35 U.S.C. §371 from PCT/US2011/042169, filed Jun. 28, 2011, published as WO 2012/012139 on Jan. 26, 2012, which claims the priority under 35 U.S.C. §119(e) of U.S. provisional application Ser. No. 61/359,942, filed Jun. 30, 2010, each of which is hereby incorporated by reference herein in its entirety for all purposes.

BACKGROUND

Compound SF-1 is disclosed and claimed in the PCT application, published as WO 2008/115,369, as a potent inhibitor of Focal Adhesion Kinase (FAK). Example 10 of the published PCT application provides the structure and a synthesis of compound SF-1, termed compound 6 therein.

SF-1

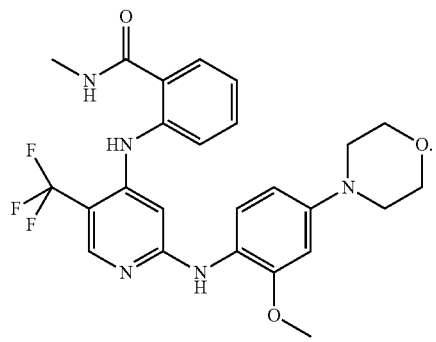

The preparation of SF-1 was carried out in two steps from available precursor materials. In a first step 2-chloro-4-iodo-5-trifluoromethylpyridine was condensed with the N-methyl amide of anthranilic acid to provide intermediate SF-Int2A.

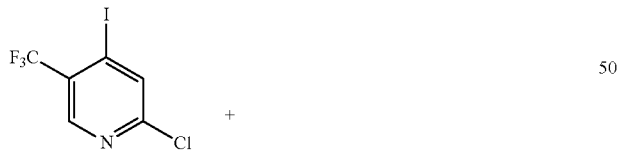

SF-Int2A

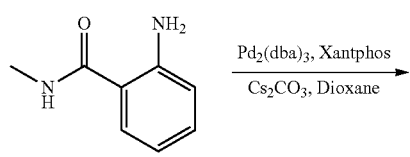

In the second step, SF-Int2A was condensed with o-methoxy-p-N-morpholinoaniline (SM3) to yield SF-1 in free base form.

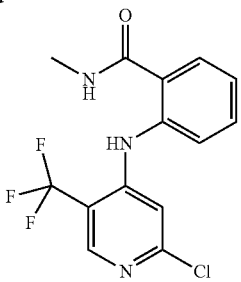

The free base form of SF-1 was subsequently converted to a hydrochloride salt and purified by recrystallization from dioxane.

Both couplings used the $Pd_2(dba)_3$/xantphos system as catalyst. $Pd_2(dba)_3$ is tris(dibenzylideneacetone)dipalladium (0). Xantphos is 4,5-bis(diphenylphosphino)-9,9-dimethylxanthene.

The efficacy of this exemplary compound as an inhibitor of Focal Adhesion Kinase (FAK) has made scaleable, high-yield synthetic routes desirable for large scale production of the compound and closely analogous compounds that may also prove to be effective inhibitors of FAK.

SUMMARY

Embodiments of the present invention are directed to improved synthetic procedures for the preparation of compound SF-Int2A and its conversion to SF-1 hydrochloride. In various embodiments, the invention provides method of synthesizing a compound of formula (I)

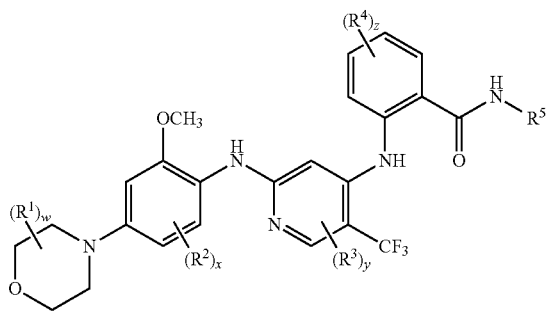

wherein $R^1$ is independently at each occurrence alkyl, aryl, cycloalkyl, heterocyclyl, aryl, or heteroaryl;

$R^2$, $R^3$ and $R^4$ are independently at each occurrence alkyl, aryl, cycloalkyl, heterocyclyl, aryl, heteroaryl, alkoxy, aryloxy, or fluoro;

$R^5$ is hydrogen, alkyl, aryl, cycloalkyl, heterocyclyl, aryl, or heteroaryl;

w is 0 to 8;
x is 0 to 3;
y is 0 to 2; and
z is 0 to 4;
including any stereoisomer thereof;
comprising contacting a compound of formula (II)

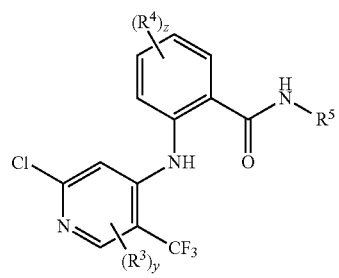

and a compound of formula (III)

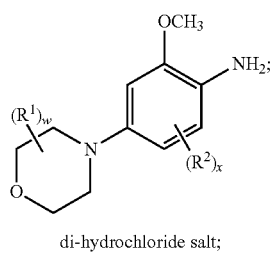

di-hydrochloride salt;

under conditions comprising:

(a) a solution of compounds (II) and (III) in a liquid hydroxylic solvent of boiling point higher than about 115 degrees C.;

(b) the compound of formula (II) being present at a concentration of no less than about 0.4 M;

(c) the compound of formula (III) being present at a concentration about 10% higher than the concentration of the compound of formula (II);

(d) a temperature in excess of about 100° C.;

(e) a duration of time of at least about 48 hours;

(f) an absence of added bases;

(g) an absence of transition metal catalysts;

followed by precipitation of the compound of formula (I) by addition of a hydrocarbon to the hydroxylic solvent following cooling of the solvent to ambient temperature, then collection of the precipitated compound.

In various embodiments, the invention further provides a method of purification of the compound of formula (I), comprising:

(a) first, dissolving and partitioning the compound of formula (I) between aqueous base and a water-immiscible organic solvent, then separating a solution of the compound of formula (I) free base in the water-immiscible organic solvent;

(b) then, adding to the solution silica gel, and optionally anhydrous magnesium sulfate, and optionally activated charcoal, then separating the solid material from the solvent to provide a purified solution of free base;

(c) then, adding a hydrocarbon to the purified solution to cause precipitation of the free base; and (d) then, collecting the precipitated free base of the compound of formula (I).

In various embodiments, the invention further provides a method of converting the free base of the compound of formula (I) to a hydrochloride salt thereof by a process comprising:

(a) contacting a first alcoholic solution of the free base and a second alcoholic solution of hydrogen chloride, then (b) adding a hydrocarbon to precipitate the compound of formula (I) hydrochloride salt; then (c) collecting the compound of formula (I) hydrochloride salt.

In various embodiments, the invention provides a method of preparing a compound of formula (II)

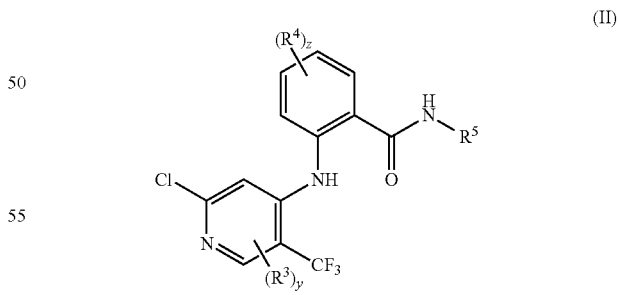

wherein $R^3$ and $R^4$ are independently at each occurrence alkyl, aryl, cycloalkyl, heterocyclyl, aryl, heteroaryl, alkoxy, aryloxy, or fluoro;

$R^5$ is hydrogen, alkyl, aryl, cycloalkyl, heterocyclyl, aryl, or heteroaryl;

y is 0 to 2; and
z is 0 to 4;

comprising:

(a) contacting a compound of formula (IV)

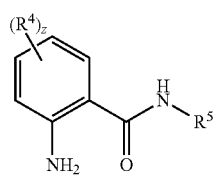

and a compound of formula (V)

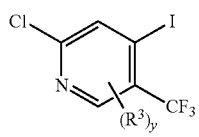

in an ethereal solvent at about 80° C.,
under conditions comprising:
(a) no more than about 0.5 wt % $Pd_2(dba)_3$;
(b) no more than about 1.5 wt % xantphos;
(c) no more than about 1.1 molar equivalents of $Cs_2CO_3$;
(d) a concentration of the compound of formula (IV) of no less than about 0.5 M;
(e) a concentration of the compound of formula (V) of no less than about 0.5 M;
(f) for a duration of about 2-3 days.

In various embodiments, the invention further provides recovering the compound of formula (II), following heating for a duration of about 2-3 days, comprising:
(a) filtering the ethereal solvent; then
(b) washing the filtrate with a water immiscible solvent to provide a filtered solution; then
(c) washing the filtered solution with aqueous base; then
(d) reducing the volume of the solution by about 90%; then
(e) adding a hydrocarbon to precipitate the compound of formula (II).

In various embodiments the invention provides a compound of formula (I), such as SF-1, prepared by a method comprising a method of the invention.

In various embodiments, the invention provides a use of a compound of formula (I) in the preparation of a medicament for treatment of inflammatory or immune disorders, or arthritis.

In various embodiments, the invention provides a method of treatment of malconditions involving inflammatory and immune responses, such as for instance arthritis in its various forms, such as osteoarthritis and rheumatoid arthritis.

DETAILED DESCRIPTION

Definitions

Figure 1:
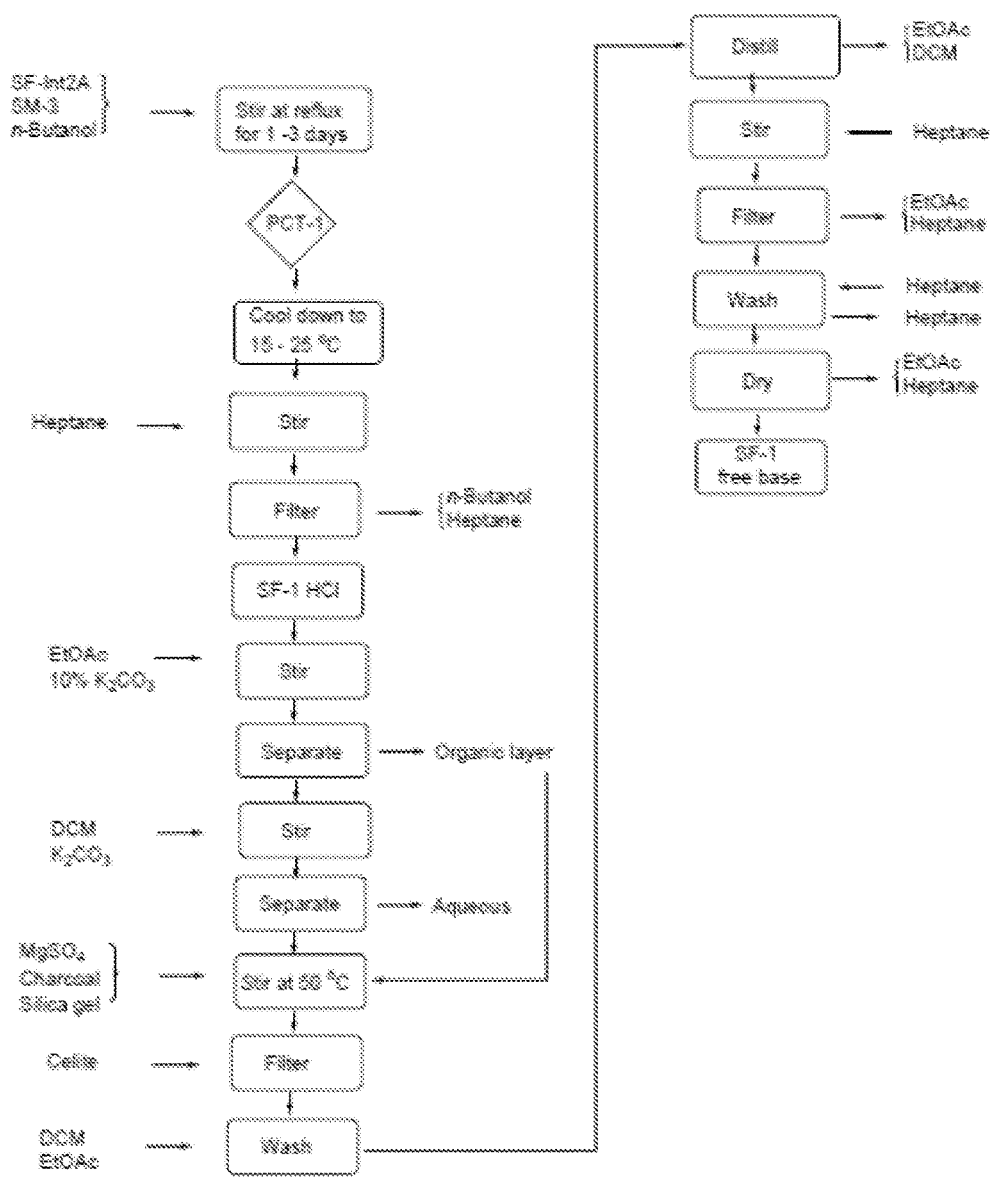
FIG. 1 is a flowchart depicting the SF-1 synthesis process.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein FAK plays a role in the biochemical mechanisms involved in the disease or malcondition such that a therapeutically beneficial effect can be achieved by acting on the kinase. "Acting on" FAK can include binding to FAK and/or inhibiting the bioactivity of FAK.

The expression "effective amount", when used to describe therapy to an individual suffering from a disorder, refers to the amount of a compound of the invention that is effective to inhibit or otherwise act on FAK in the individual's tissues wherein FAK involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

DESCRIPTION

Synthesis of SF-1

The synthetic pathway to SF-1 that was selected involves two successive coupling reactions, as shown:

Scheme 1: Overall Synthetic Route to SF-1

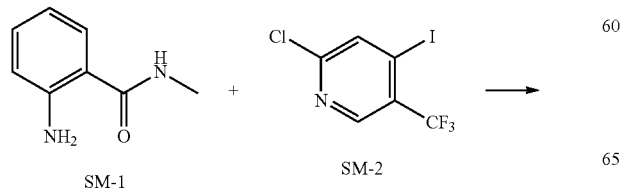

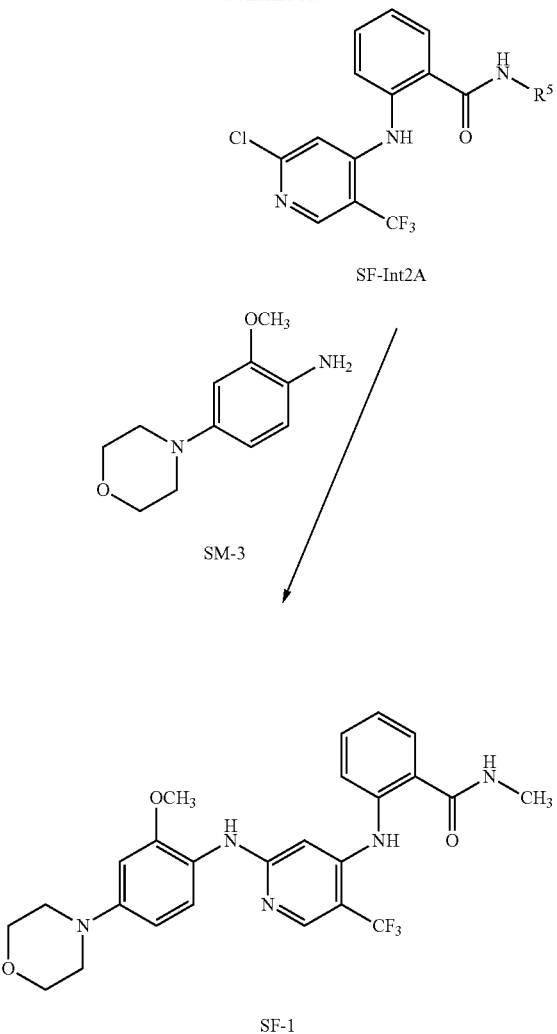

In the method disclosed in WO 2008/115,369 both coupling steps were carried out using the palladium transition metal catalyst $Pd_2(dba)_3$/xantphos.

In various embodiments, the present invention provides an improved method for the final synthetic transformation of a compound exemplary for formula (I), termed SF-1 (compound 6 of WO 2008/115,369), shown in Scheme 2, below.

Scheme 2: Optimized Synthesis of SF-1

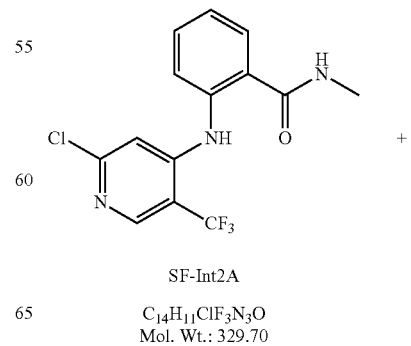

SF-Int2A $C_{14}H_{11}ClF_3N_3O$
Mol. Wt.: 329.70

-continued

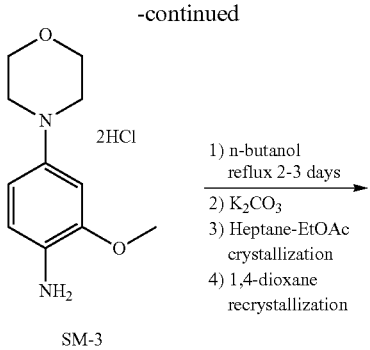

SM-3

C₁₁H₁₈ClF₂N₂O₂
Mol. Wt.: 281.18

1) n-butanol
   reflux 2-3 days
2) K₂CO₃
3) Heptane-EtOAc
   crystallization
4) 1,4-dioxane
   recrystallization

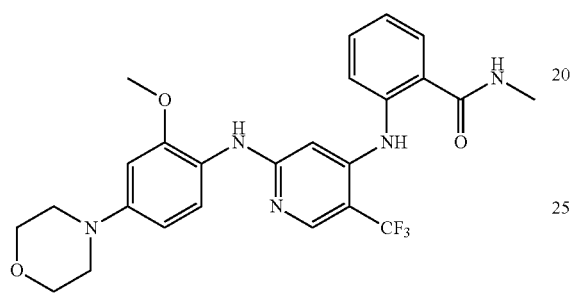

SF-1 free base

C₂₅H₂₆F₃N₅O₃
Mol. Wt.: 501.50

In various embodiments, the invention provides a method of synthesizing a compound of formula (I)

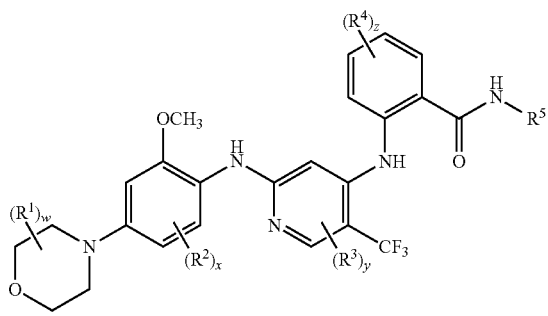

wherein

R¹ is independently at each occurrence alkyl, aryl, cycloalkyl, heterocyclyl, aryl, or heteroaryl;

R², R³ and R⁴ are independently at each occurrence alkyl, aryl, cycloalkyl, heterocyclyl, aryl, heteroaryl, alkoxy, aryloxy, or fluoro;

R⁵ is hydrogen, alkyl, aryl, cycloalkyl, heterocyclyl, aryl, or heteroaryl;

w is 0 to 4;

x is 0 to 3;

y is 0 to 2; and z is 0 to 4;

including any stereoisomer thereof;

comprising contacting a compound of formula (II)

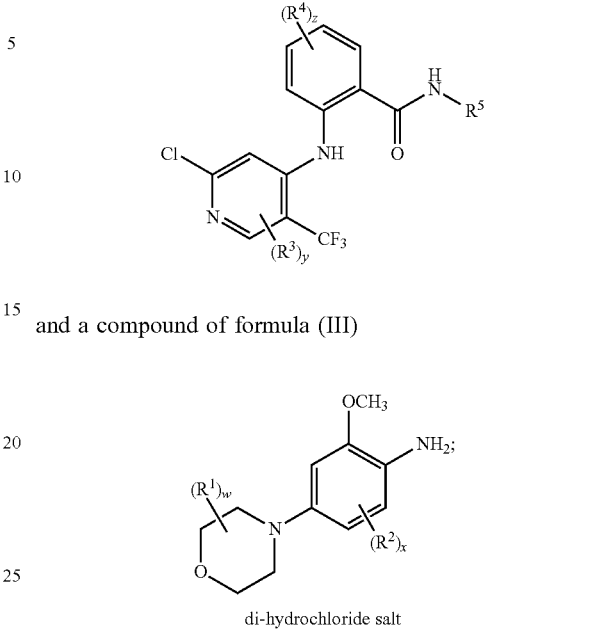

and a compound of formula (III)

di-hydrochloride salt under conditions comprising:

(a) a solution of compounds (II) and (III) in a liquid hydroxylic solvent of boiling point higher than about 115 degrees C.;

(b) the compound of formula (II) being present at a concentration of no less than about 0.4 M;

(c) the compound of formula (III) being present at a concentration about 10% higher than the concentration of the compound of formula (II);

(d) a temperature in excess of 100° C.;

(e) a duration of time of at least about 48 hours;

(f) an absence of added bases;

(g) an absence of transition metal catalysts;

followed by precipitation of the compound of formula (I) by addition of a hydrocarbon to the hydroxylic solvent following cooling of the solvent to ambient temperature, then collection of the precipitated compound.

For example, the hydroxylic solvent can be n-butanol, methoxyethanol, or ethoxyethanol. More specifically, the hydroxylic solvent can be n-butanol.

In various embodiments, the concentration of the compound of formula (II) can be about 0.5 M.

In various embodiments, the temperature can be about 118-166° C., i.e., at or near the boiling point of a hydroxylic solvent such as n-butanol, methoxyethanol, or ethoxyethanol. In various embodiments the reaction can be carried out at the reflux point of the hydroxylic solvent chosen.

Various hydrocarbons can be used to bring about precipitation of the reaction product. For example, the hydrocarbon can be heptane.

In various embodiments, the yield of the compound of formula (I) can be at least about 75%. In various embodiments, the purity of the compound of formula (I) can be at least about 98%.

More specifically, the compound of formula (I) can be a compound of formula

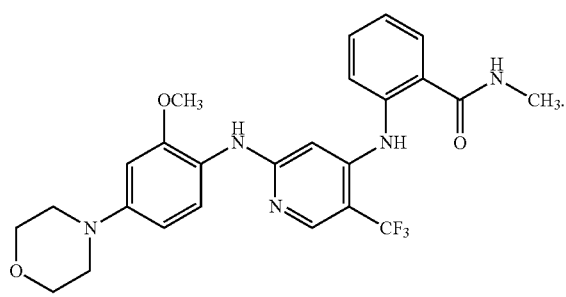 [SMILES: CNC(=O)c1ccccc1Nc1cc(Nc2ccc(N3CCOCC3)cc2OC)ncc1C(F)(F)F]

Accordingly, the compound of formula (II) can be a compound of formula

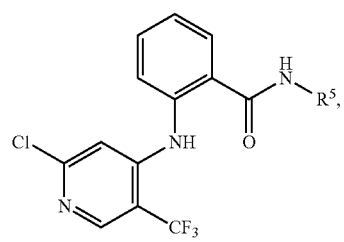

or the compound of formula (III) can be a compound of formula

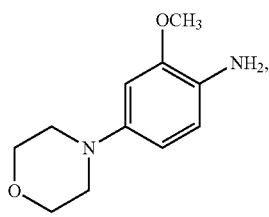 [SMILES: COc1cc(N2CCOCC2)ccc1N]

or both.

Coupling of the 2-chloropyridine derivative SF-Int2A with aniline derivative SM-3 (in the form of a stoichiometically defined dihydrochloride salt) yields SF-1 hydrochloride, which is recovered as the free base form following workup. The free base was obtained in greater than 70% yield of 99% pure material prior to the final step of recrystallization from 1,4-dioxane. Recrystallization yielded material of greater than 99.5% purity in greater than 85% yield.

Conversion to the HCl salt was then carried out to provide the active pharmaceutical ingredient in the form of a pharmaceutically acceptable salt.

Optimization of various parameters for this coupling reaction was studied. The art coupling reaction used the transition metal catalyst $Pd_2(dba)_3$/xantphos in 1,4-dioxane solvent in the presence of $Cs_2CO_3$ base. The inventors herein have unexpectedly discovered that use of an alcoholic solvent, rather than an ethereal solvent such as 1,4-dioxane, can bring about the coupling reaction in good yield and purity in the complete absence of any catalyst, particularly in the absence of the expense palladium transition metal catalyst $Pd_2(dba)_3$/xantphos.

Investigation of alcoholic (hydroxylic) solvent with a range of boiling points in excess of 100° C. was investigated. Alcohols such as n-butanol, methoxyethanol, ethoxymethanol, n-hexanol, and cyclohexanol, and non-alcohols DMF, DMSO, and diethyleneglycol dimethylether were investigated as reaction solvents. The SF-Int2A and SM-3 reagents were dissolved in the solvent at approximately 0.5 M concentration, with a 10% molar excess of the SM-3, and the solvents were heated to reflux except in the cases of DMSO and DMF, where the reactions were heated to 135° C. Results are shown in Table 1, below.

TABLE 1

Study of solvent on yield of SF-1

| | | | 5 hrs (A %) | | | 20 hrs (A %) | | | 44 hrs (A %) | | |
|---|---|---|---|---|---|---|---|---|---|---|---|
| Entry | Material Name | BP | SF-Int-2A | SM-1 | Product | SF-Int2A | SM-1 | Product | SF-int2A | SM-3 | Product |
| 1 | DMSO | 189 | N/A | N/A | N/A | | | | | | |
| 2 | 2-Ethoxyethanol | 135 | 32.7 | 6.08 | 51.24 | 21.12 | | 76.7 | 19.29 | 0 | 77.01 |
| 3 | 2-Methoxyethanol | 124-125 | 15.57 | 10.99 | 72.24 | 3.63 | 4.3 | 89.17 | 0 | 1.91 | 91.62 |
| 4 | n-Butanol | 116-118 | 36.82 | 17.15 | 42.76 | 8 | 5.9 | 81.46 | 1.18 | 5.1 | 87.36 |
| 5 | DMF | 153 | 35.14 | N/A | 39.45 | 25.7 | N/A | 38.9 | 11.44 | N/A | 36.56 |

As seen in Table 1, the three most favorable solvents were found to be n-butanol, 2-ethoxyethanol, and 2-methoxyethanol. In another experiment using cyclohexanol, n-hexanol, and diethyleneglycol dimethyl ether, lower yields were observed. In a separate experiment, little or no product was observed to be formed in DMSO or DMF. In the alcohols, there was no significant difference in product yield when the reaction was carried out under ambient atmosphere or under nitrogen gas atmosphere.

The reaction in n-butanol was carried out on a 40 gm scale; see Example 1, below.

In various embodiments, the invention provides a method for further purification of the compound of formula (I), comprising:

(a) first, dissolving and partitioning the compound of formula (I) between aqueous base and a water-immiscible organic solvent, then separating a solution of the compound of formula (I) free base in the water-immiscible organic solvent;

(b) then, adding to the solution silica gel, and optionally anhydrous magnesium sulfate, and optionally activated charcoal, then separating the solid material from the solvent to provide a purified solution of free base;

(c) then, adding a hydrocarbon to the purified solution to cause precipitation of the free base; and (d) then, collecting the precipitated free base of the compound of formula (I).

In various embodiments, the aqueous base comprises aqueous carbonate, for example, 10% aqueous potassium carbonate. In various embodiments, the water immiscible solvent can be ethyl acetate, dichloromethane, or any mixture thereof.

In various embodiments, separating the solid material (silica gel, charcoal, magnesium sulfate) can be carried out by a process comprising filtration or centrifugation, or both.

In various embodiments, the purified free base can be precipitated from the solution by addition of a hydrocarbon, such as heptane. The precipitated purified free base can be collected by a process that comprises filtration or centrifugation, or both.

In various embodiments, the free base of formula (I) is a compound of formula

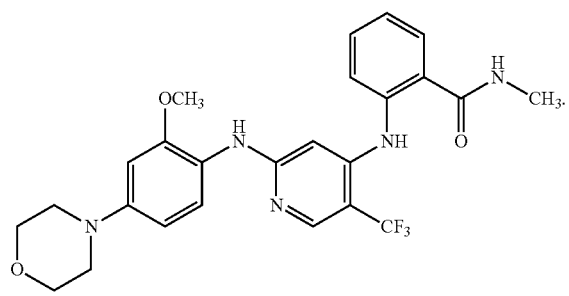 [SMILES: CNC(=O)c1ccccc1Nc1cc(Nc2ccc(N3CCOCC3)cc2OC)ncc1C(F)(F)F]

In various embodiments, the yield of the compound of formula (I) can be at least about 70%, and the purity of the compound of formula (I) can be at least about 98%.

Accordingly, further purification of the crude reaction product, in particular to remove color bodies, can be carried out by treatment of a solution of SF-1 free base with solid absorbents. As shown in FIG. 1, a flow chart of an optimized synthetic process for decolorized SF-1 free base, the product resulting from the above-described reaction, believed to be a hydrochloride salt of SF-1 as existing in the reaction solvent due to the formation of an equivalent of HCl from the reaction, can be converted to free base form by partition between a water-immiscible organic solvent, e.g., ethyl acetate, and an aqueous base such as carbonate solution. The SF-1 free base, or the corresponding free base of a compound of formula (I), partitions into the organic phase. The aqueous phase can be backwashed with the same or a different water-immiscible organic solvent, e.g., dichloromethane (DCM).

Then, the combined organic phases can be dried and decolorized by treatment with silica gel, optionally with anhydrous magnesium phosphate, optionally with activated charcoal. For example, it was found that on a 40 gm scale (i.e., 40 gm of SF-Int2A), addition of about 200 gm of silica to the organic extract described above, was effective in decolorizing the solution. Addition of about 40 gm activated charcoal improved the effectiveness of the decolorization, and 40 gm anhydrous magnesium sulfate could be used to thoroughly dry the solution. See Example 2, below.

An embodiment of an inventive method is shown in FIG. 1. The two reactants are stirred together in a hydroxylic solvent such as n-butanol at reflux for 2-3 days. The progress of the reaction can be monitored by HPLC. Following completion of the reaction, the reaction mixture is cooled and a hydrocarbon such as heptane is added to precipitate the reaction product. The precipitate is filtered, then is partitioned between a water-immiscible solvent such as ethyl acetate and aqueous base, such as potassium carbonate, to liberate the free base form. The aqueous phase can be further extracted with the same or different organic water-immiscible solvent, such as dichloromethane (DCM). The combined organic extracts are then treated with silica gel, for example with about 5× the weight of the starting material of silica gel, which is then filtered to provide a decolorized solution of the SF-1 free base. Optionally, charcoal, and/or anhydrous magnesium sulfate, are added. Then, the solution is filtered, for example through Celite, and the solvent(s) removed from the filtrate to provide SF-1 free base.

The SF-1 or other compound of formula (I) herein prepared by the inventive method can be further purified by recrystallization. In various embodiments of the invention, recrystallization is carried out in 1,4-dioxane.

The purification of SF-1 free base by recrystallization from 1,4-dioxane was evaluated using various ratios of compound to solvent, with respect to purity and yield of the recrystallized product. Individual procedures are shown in Example 3, and Table 2, below, shows the yield and purity of the products obtained under the conditions specified in Example 3.

TABLE 2

Recrystallization of SF-1 free base from 1,4-dioxane

| Entry | SF-1:dioxane (w/v) (Yield %) | Results (A %) −8.57 min* | −8.79 min* | SF-1 Free Base |
|---|---|---|---|---|
| 1 | 1/2 (98% yield) | 0.72 | 0.96 | 98.32 |
| 2 | 1/3 (97% yield) | N/A | 0.87 | 98.13 |
| 3 | 1/5 (93% yield) | N/A | 0.53 | 99.47 |
| 4 | 1/8 (89% yield) | N/A | 0.24 | 99.76 |
| 5 | 1/10 (87% yield) | N/A | 0.24 | 99.76 |

As can be seen, variations in purity and yield were observed using variants of the 1,4-dioxane recrystallization procedures, and a higher purity was obtained using somewhat lower concentrations of the crude material in the recrystallization solvent, with only a slight reduction in yield.

Conversion of SF-1 to its hydrochloride salt, and additional purification, were achieved according to various embodiments of the inventive method. In various embodiments, the invention provides a method further comprising converting the free base of the compound of formula (I) to a hydrochloride salt thereof by a process comprising:

(a) contacting a first alcoholic solution of the free base and a second alcoholic solution of hydrogen chloride, then (b) adding a hydrocarbon to precipitate the compound of formula (I) hydrochloride salt; then (c) collecting the compound of formula (I) hydrochloride salt.

For example, the first alcoholic solution can be in ethanol, or the second alcoholic solution can be in isopropanol, or both. In various embodiments, the hydrocarbon can be heptane.

In various embodiments, the hydrochloride salt of the compound of formula (I) can be a mono-hydrochloride salt, i.e., a stoichiometrically defined salt of a pharmaceutically acceptable identity.

In various embodiments, the hydrochloride salt of the compound of formula (I) can be further purified by recrystallizing the compound, for instance, from 1,4-dioxane. The compound of formula (I) hydrochloride salt obtained by a method of the invention can of at least 99% purity, or of at least 99.5% purity, such as measured by HPLC area percentage. A recrystallization yield of at least about 85% can be obtained. The overall yield of formula (I) hydrochloride salt can be at least about 70%, with a purity of at least about 97%. The compound of formula (I) can be SF-1 hydrochloride, i.e., a compound of formula

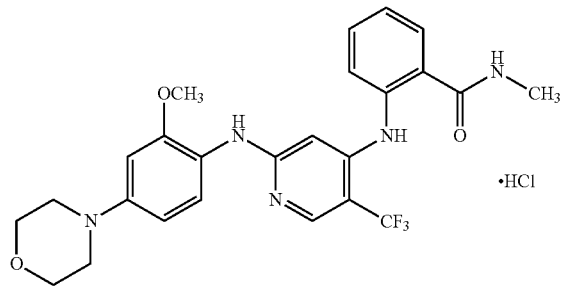 [SMILES: CNC(=O)c1ccccc1Nc1cc(Nc2ccc(N3CCOCC3)cc2OC)ncc1C(F)(F)F ; Cl]

which is obtained in at least about 99% purity and at least about 60% overall yield based upon SF-Int2A.

Figure 2:
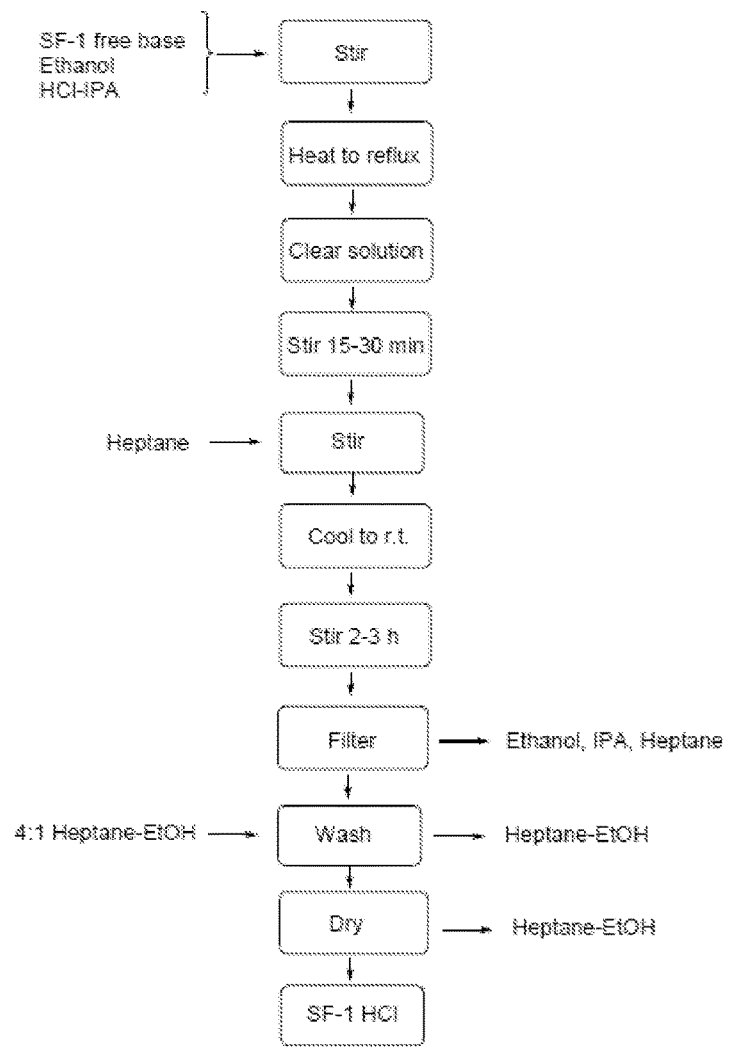
FIG. 2 is a flowchart of the embodiment of a hydrochloride salt preparative portion of a method of the invention.

Example 4, below, provides experimental details for the preparation of a hydrochloride salt of a compound of formula (I). FIG. 2, is a flowchart of the embodiment of a hydrochloride salt preparative portion of a method of the invention.

Synthesis of SF-1 Analogs

In various embodiments, the invention provides a method of synthesis of other compounds of formula (I) analogous to SF-1.

For example, the inventive method can be applied to the synthesis of a compound of formula SF-2:

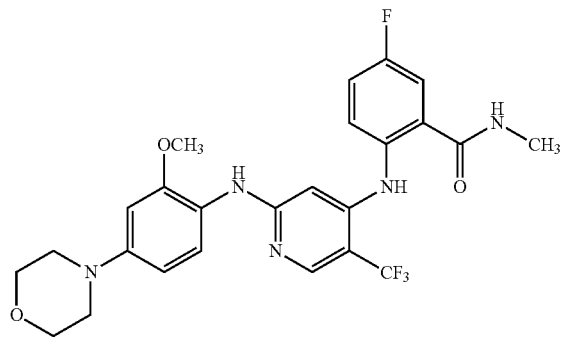

or any pharmaceutically acceptable salt thereof. More specifically, the synthesis of this kinase inhibitor can be carried out as detailed above for compound SF-1, provided that for compound SM-1, a compound of the following formula replaces SM-1 with SM-1A in carrying out the first step as shown above in Synthetic Scheme 1.

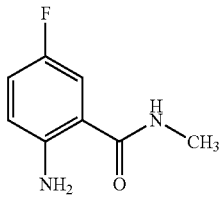

This starting material can be converted to compound (II) as shown below, then converted to a compound of formula SF-2 using the methods disclosed and claimed herein.

Synthesis of SF-Int2A

In various embodiments, the invention provides a method of preparing a compound of formula (II)

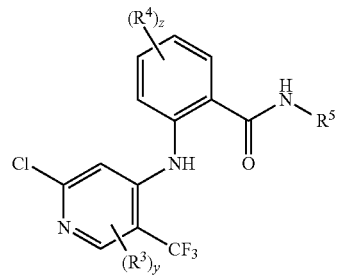

wherein $R^3$ and $R^4$ are independently at each occurrence alkyl, aryl, cycloalkyl, heterocyclyl, aryl, heteroaryl, alkoxy, aryloxy, or fluoro;

$R^5$ is hydrogen, alkyl, aryl, cycloalkyl, heterocyclyl, aryl, or heteroaryl;

y is 0 to 2; and z is 0 to 4; comprising:

(a) contacting a compound of formula (IV)

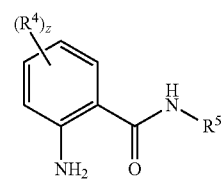

and a compound of formula (V)

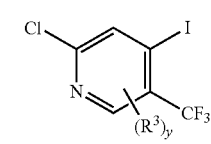

in an ethereal solvent at about 80° C.,
under conditions comprising:
(a) no more than about 0.5 wt % Pd2(dba)3;
(b) no more than about 1.5 wt % xantphos;
(c) no more than about 1.1 molar equivalents of $Cs_2CO_3$;
(d) a concentration of the compound of formula (IV) of no less than about 0.5 M;
(e) a concentration of the compound of formula (V) of no less than about 0.5 M;
(f) for a duration of about 2-3 days.

For instance, the ethereal solvent can be 1,4-dioxane.

In various embodiments, the method further comprises recovering the compound of formula (II) by a method comprising:

(a) filtering the ethereal solvent; then
(b) washing the filtrate with a water immiscible solvent to provide a filtered solution; then
(c) washing the filtered solution with aqueous base; then
(d) reducing the volume of the solution by about 90%; then
(e) adding a hydrocarbon to precipitate the compound of formula (II).

For example, the water-immiscible solvent can be ethyl acetate.

For example, the aqueous base can be aqueous carbonate or bicarbonate.

For example, the hydrocarbon can be heptane.

In various embodiments, the compound of formula (IV) can be

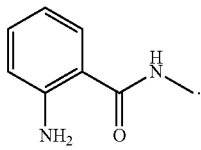

In various embodiments, the compound of formula (V) can be

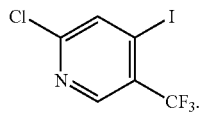

In various embodiments, the purity of the compound of formula (II) can be at least about 99%, and the yield of the compound of formula (II) can be at least about 90%.

Exemplary experimental details are provided in Example 5, below.

In various embodiment, the invention provides a method of preparing a compound of formula (II) of the formula:

SF-Int2A

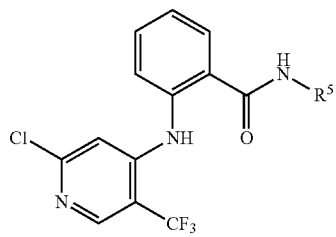

accordingly to the procedures outlined below.

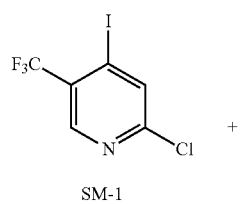

SM-1

$C_6H_2ClF_3IN$
Mol. Wt.: 307.44

+

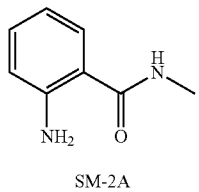

SM-2A $C_8H_{10}N_2O$
Mol. Wt.: 150.18

-continued

1) $Pd_2(dba)_3$ (0.5 mol %)
Xantphos (1.5 mol %)
$Cs_2CO_3$ (1.0 eq.), 1,4-dioxane
80° C., 2-3 days 2) aq. NaCl, aq. $NaHCO_3$
3) Heptane-EtOAc recrystallization

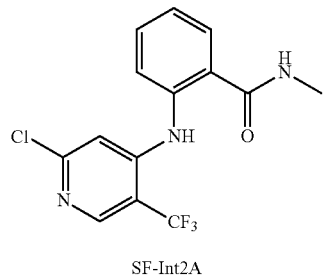

SF-Int2A $C_{14}H_{11}ClF_3N_3O$
Mol. Wt.: 329.70

It was surprisingly discovered by the inventors herein that the selection of base used in the reaction greatly influenced the time to reaction completion. Table 3, below, shows time points in a comparison study of $Cs_2CO_3$ and $K_2CO_3$ (both solid and aqueous) in the coupling reaction of SM-1 and SM-2A.

TABLE 3

Time course of coupling reaction in presence of various bases

| Time | $Cs_2CO_3$ (% Yield) | $K_2CO_3$ (% Yield) | Aqueous $K_2CO_3$ (% Yield) |
|---|---|---|---|
| 3 h | 96.5 | 14 | 24 |
| 18 h | 100 | 61.4 | 49 |
| 42 h | N/A | 92 | 60 |
| 66 h | N/A | 100 | 69 |

As can be seen, conversion is surprisingly complete using $Cs_2CO_3$ after only 18 hours, while solid $K_2CO_3$ requires 66 hours, and the reaction is only about 69% done after 66 hours with aqueous $K_2CO_3$.

Further studies were conducted to example the molar ratio of $Cs_2CO_3$ base to starting material SM-1. Tables 4a and 4b respectively show the yield and purity of product SF-Int2A at time points 3 hours and 18 hours over a range of relative molar quantitites.

TABLE 4a

Conversion of SM-1 at 3 Hours with Various Molar Quantities of Base

| Entry | Ratio SM-1:$Cs_2CO_3$ | Reaction time (h) | Product (%) | SM-1 (%) | Impurity (%) |
|---|---|---|---|---|---|
| 1a | 1:1.0 | 3 | 97.8 | 1.5 | 0.65 |
| 2a | 1:1.2 | 3 | 97.7 | 1.0 | 0.82 |
| 3a | 1:1.4 | 3 | 96.4 | 0.88 | 2.28 |
| 4a | 1:1.6 | 3 | 95.0 | 1.0 | 3.11 |
| 5a | 1:1.8 | 3 | 94.3 | 0.86 | 4.85 |
| 6a | 1:2.0 | 3 | 96.2 | 0.96 | 2.85 |

TABLE 4a-continued

Conversion of SM-1 at 3 Hours with Various Molar Quantities of Base

| Entry | Ratio SM-1:Cs$_2$CO$_3$ | Reaction time (h) | Product (%) | SM-1 (%) | Impurity (%) |
|---|---|---|---|---|---|
| 7a | 1:2.2 | 3 | 93.4 | 1.47 | 5.2 |
| 8a | 1:2.4 | 3 | 79.2 | 0 | 20.7 |

TABLE 4b

Conversion of SM-1 at 18 Hours with Various Molar Quantities of Base

| Entry | Ratio SM-1:Cs$_2$CO$_3$ | Reaction time (h) | Product (%) | SM-1 (%) | Impurity (%) |
|---|---|---|---|---|---|
| 1b | 1:1.0 | 18 | 95.4 | 0.45 | 4.2 |
| 2b | 1:1.2 | 18 | 87.6 | 0 | 12.4 |
| 3b | 1:1.4 | 18 | 91.15 | 0 | 8.85 |
| 4b | 1:1.6 | 18 | 90.18 | 0 | 9.82 |
| 5b | 1:1.8 | 18 | 88.89 | 0 | 11.11 |
| 6b | 1:2.0 | 18 | 90.67 | 0 | 9.32 |
| 7b | 1:2.2 | 18 | 76.47 | 0 | 23.52 |
| 8b | 1:2.4 | 18 | 76.48 | 0 | 23.52 |

Experiments were conducted to determine the minimum molar ratio of catalyst to reactants under the reaction conditions previously examined. Referring to Table 5, entries 1a-5a, and 1b-5b correspond with the short time and longer time points of reactions in Tables 4a and 4b with varying amounts of Cs$_2$CO$_3$ and the mole % of catalyst shown. Time points are at 4 hours and 18 hours.

TABLE 5

Screening of Catalyst Mole %

| Entry | Ratio SM-1:Pd catalyst | Reaction time (h) | Product (%) | SM-1 (%) | Impurity* (%) |
|---|---|---|---|---|---|
| 1a | 2 mol % | 4 | 96 | 2.6 | 0.9 |
| 2a | 1 mol % | 4 | 81 | 36 | 0.7 |
| 3a | 0.5 mol % | 4 | 63 | 36 | 0.7 |
| 4a | 0.1 mol % | 4 | 6** | 94** | 0 |
| 5a | 0.05 mol % | 4 | 10 | 90 | 0 |
| 1b | 2 mol % | 18 | 88 | 0 | 12 |
| 2b | 1 mol % | 18 | 95 | 0 | 5 |
| 3b | 0.5 mol % | 18 | 97 | 0 | 3 |
| 4b | 0.1 mol % | 18 | 17** | 83** | 3 |
| 5b | 0.05 mol % | 18 | 87 | 0 | 12 |

*Note: Impurity = RRT 0.77
**Note: The conversion was low due to a problem with stirring in this experiment.

In Tables 5 and 6, the second column indicates the mole % of the Pd$_2$(dba)$_3$/xantphos catalyst system per mole of SM-1.

The results indicate that no significant advantage in yield or purity is achieved when using in excess of 0.5 mol % of the Pd$_2$(dba)$_3$/xantphos catalyst system in this conversion.

Table 6 shows a second series of experiments using 0.5 mol % and less of the catalyst system in this conversion, using 1 molar equivalent Cs$_2$CO$_3$ in dioxane.

TABLE 6

Product Yield and Purity versus Catalyst Ratio

| Entry | Ratio SM-1:Pd catalyst | Reaction time (h) | Product (%) | SM-1 (%) | Impurity* (%) |
|---|---|---|---|---|---|
| 1a | 0.50 mol % | 14 | 96.47 | 2.58 | 0.94 |
| 2a | 0.25 mol % | 14 | 95.46 | 4.54 | N/A |
| 3a | 0.10 mol % | 14 | 84.69 | 15.3 | N/A |
| 1b | 0.50 mol % | 24 | 98.77 | 0 | 1.22 |
| 2b | 0.25 mol % | 24 | 98.12 | 1.88 | N/A |
| 3b | 0.10 mol % | 24 | 91.67 | 8.33 | N/A |

Yields and purities are seen to drop off somewhat when reducing the amount of catalyst below 0.5 mol %.

Table 7 shows the results of a solvent selection study.

TABLE 7

Effect of Solvent Selection on Product Yield and Purity

| Entry | Solvent | Reaction time (h) | Yield (%) of Product$^a$ | SM-1 (%) | Impurities (%) |
|---|---|---|---|---|---|
| 1a | 1,4-Dioxane | 3 | 94 | 5.8 | 0 |
| 2a | n-Butanol | 3 | 79 | 0 | 21 |
| 3a | Ethylene glycol | 3 | 0 | 0 | 100$^b$ |
| 4a | DMF | 3 | 65 | 35 | 0 |
| 5a | DMSO | 3 | 58 | 26 | 14$^c$ |
| 1b | 1,4-Dioxane | 18 | 88 | 0 | 12 |
| 2b | n-Butanol | 18 | 29 | | 56.5$^d$ |
| 3b | Ethylene glycol | 18 | N/A | N/A | N/A |
| 4b | DMF | 18 | 76 | 13 | 11$^c$ |
| 5b | DMSO | 18 | 87 | 0 | 12 |

At a 3 hour time point, reaction in dioxane is virtually complete, and is very clean, while reactions conducted in solvents n-butanol, ethylene glycol, DMF, and DMSO give lower yields and higher levels of impurities.

A detailed synthetic procedure using these parameters is provided in Example 5, below.

In various embodiments, the invention provides a compound of formula (I) of claim 1 or a pharmaceutically acceptable salt thereof prepared by a method comprising a method of the invention. For example, an embodiment provides the compound of formula

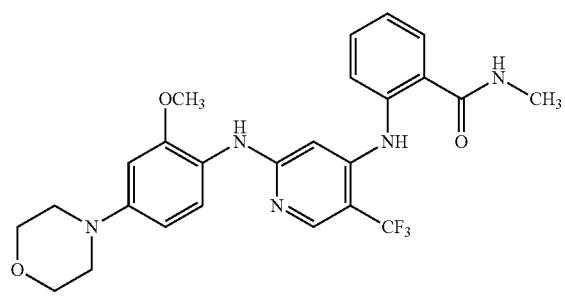 [SMILES: CNC(=O)c1ccccc1Nc1cc(Nc2ccc(N3CCOCC3)cc2OC)ncc1C(F)(F)F]

or a compound of formula

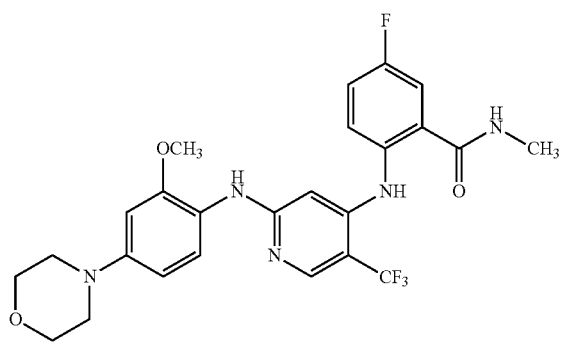 [SMILES: CNC(=O)c1cc(F)ccc1Nc1cc(Nc2ccc(N3CCOCC3)cc2OC)ncc1C(F)(F)F]

or a pharmaceutically acceptable salt thereof. More specifically, the pharmaceutically acceptable salt can be a hydrochloride salt.

Use of SF-L and Analogs in Treatment of Inflammatory and Immune Disorders and of Arthritis The inhibition of Focal Adhesion Kinase (FAK) is believed by inventors herein to be an effective therapy in the treatment of an inflammatory or immune disorder, or arthritis.

Accordingly, various embodiments of the invention provide the use of a compound of formula (I) in preparation of a medicament for treatment of an inflammatory or immune disorder, or arthritis.

In various embodiments, the invention provides a method of treatment of an inflammatory or immune disorder, or arthritis, in a patient comprising administering to the patient an effective dose of a compound of formula (I) at a frequency and for a duration of time to provide a beneficial effect to the patent. For example, the compound of formula (I) can be

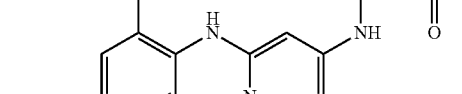

or a compound of formula

or a pharmaceutically acceptable salt thereof.

EXAMPLES

Example 1

Synthesis of SF-1 in n-butanol

Figure 3:
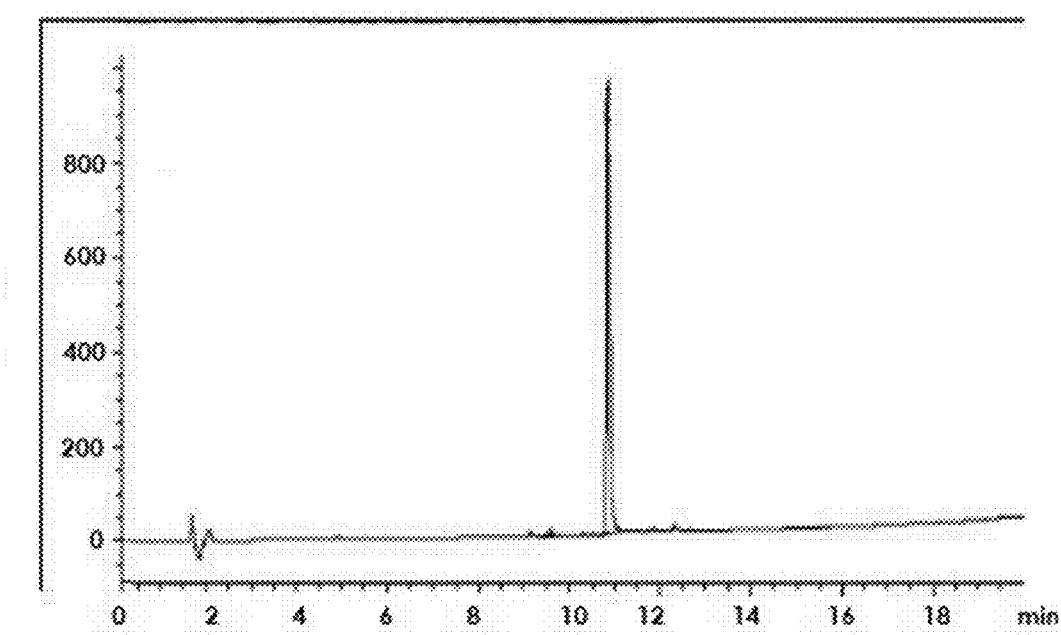
FIG. 3 is a graph depicting Synthesis of SF-1 in n-butanol

Purity was determined by HPLC (FIG. 3).

| OP step# | Material Name | Lot# | MW | equiv | mmol | W (g) | V (mL) |
|---|---|---|---|---|---|---|---|
| 1 | SF-Int2A | 1779-56-15 | 329.7 | 1 | 121.32 | 40.00 | |
| 1 | SM-3 | LB-008-125C | 281.18 | 1.1 | 133.45 | 37.52 | |
| 1 | n-Butanol | | | | | | 240 |
| 4 | Heptane | | | | | | 480 |
| 5 | EtOAc | | | | | | 100 |
| 5 | Heptane | | | | | | 100 |
| 5 | Heptane | | | | | | 100 |
| 6 | EtOAc | | | | | | 1200 |
| 6 | $K_2CO_3$ | | 138.21 | 5 | 606.61 | 84 | |
| 6 | Water | | 18.01 | | | | 800 |
| 8 | $K_2CO_3$ | | 138.21 | | | 20 | |
| 8 | DCM | | | | | | 800 |
| 10 | Charcoal | | | | | 40 | |
| 10 | $MgSO_4$ | | | | | 40 | |
| 10 | Silica gel | | | | | 200 | |
| 12 | Celite | | | | | 50 | |
| 12 | EtOAc | | | | | | 1200 |
| 12 | DCM | | | | | | 800 |
| 14 | Heptane | | | | | | 600 |
| 16 | Heptane | | | | | | 300 |

Procedure

| Op# | Operation |
|---|---|
| 1 | Charge SF-Int2A (40 g, 121 mmol), SM-3 (37.52 g, 133 mmol) and n-butanol (240 mL). |
| 2 | Heat the mixture to gentle reflux for 2-3 days under nitrogen atmosphere. |

| Op# | Operation |
|---|---|
| 3 | Check the reaction by HPLC. After 18 h, there was 13.81% SF-Int2A left. After 48 hour, there was 3.18% SF-Int2A left. |
| 4 | Cool down to 15-25° C. Stir the mixture overnight. Charge heptane (480 mL). Stir the mixture at room temperature for about 1 hour. |
| 5 | Filter the precipitate formed. Wash the cake with EtOAc/heptane (1:1, 200 mL) and then heptane (100 mL). |
| 6 | Charge the cake with 1200 mL of EtOAc and 10% aq. $K_2CO_3$ (800 mL) to the reactor. |
| 7 | Separate the layers. Keep the aqueous layer in the reactor. |
| 8 | Charge 20 g of $K_2CO_3$ powder to the reactor. Stir until clear. Charge 800 mL of DCM to the reactor. Stir the mixture for 10-20 min. |
| 9 | Separate the layers. Combine the organic layers. |
| 10 | Charge 40 g of Charcoal and 40 g of $MgSO_4$ and 200 g of silica gel to the organic layer. |
| 11 | Stir the organic layer at gentle reflux point for about 30 min. |
| 12 | Cool the mixture down to room temperature and filter through Celite pad (50 g). Wash the cake with EtOAc/DCM (3:2, 2000 mL). |
| 13 | Distill the solvent to ~200 to 250 mL of volume left. |
| 14 | Charge heptane (600 mL) with stirring. |
| 15 | Cool the mixture to room temperature with stirring. Stir the mixture at rt overnight. |
| 16 | Filter the precipitate formed and wash the cake with heptane (300 mL). |
| 17 | Dry the cake to give rise to 44 g (72.5%) of yellow powder. HPLC 1779-76-17S: Purity 98.9%. |

Example 2

Decolorization of SF-1 Free Base

Procedure A:

| Op# | Operation | Note |
|---|---|---|
| 1 | Charge SF-1 HCl (2 g), EtOAc (60 mL). | Sample from 1779-58-5 |
| 2 | Charge 30 mL of 10% $K_2CO_3$ aqueous solution to the reactor with stirring. Continue to stir the mixture for 1 to 2 hours. | |
| 3 | Separate the layers. Keep the organic layer in the reactor. | |
| 4 | Charge 2 g of $MgSO_4$ and 20 g of silica gel to the reactor. | |
| 5 | Charge dichloromethane (40 mL) to the reactor. | |
| 6 | Heat the mixture to 50° C. for 30 min. | |
| 7 | Cool the mixture to 15-25° C. | |
| 8 | Filter through Celite (5 g). Wash the cake with 50 mL of mixture DCM/EtOAc (2:3). | |
| 9 | Distill the solvent to 5-7.5 mL. Add heptane (25-32.5 mL) to the reactor. | |
| 10 | Cool the mixture to 15-25° C. Stir the mixture for 2-3 hours. | |
| 11 | Filter the precipitate formed. Wash the cake with heptane (20 mL). | |
| 12 | Dry the cake under vacuum to give 1.0 g of yellow solid, yield 57%, purity 98.7%. | |

Procedure B:

| Op# | Operation | Note |
|---|---|---|
| 1 | Charge SF-1 HCl (2 g), EtOAc (60 mL). | Sample from 1779-58-5 |
| 2 | Charge 30 mL of 10% $K_2CO_3$ aqueous solution to the reactor with stirring. Continue to stir the mixture for 1 to 2 hours. | |
| 3 | Separate the layers. Keep the organic layer in the reactor. | |
| 4 | Charge 2 g of $MgSO_4$ and 2 g of charcoal to the reactor. | |
| 5 | Heat the mixture to 50° C. for 30 min. | |
| 6 | Cool the mixture to 15-25° C. | |
| 7 | Filter through Celite (5 g). Wash the cake with EtOAc (60 mL). | |
| 8 | Distill the solvent to 5-7.5 mL. Add heptane (25-32.5 mL) to the reactor. | |
| 9 | Cool the mixture to 15-25° C. Stir the mixture for 2-3 hours. | |
| 10 | Filter the precipitate formed. Wash the cake with heptane (20 mL). | |
| 11 | Dry the cake under vacuum to give 1.2 g of yield solid, yield 69%, purity 98.6%. | |

Procedure C:

| Op# | Operation | Note |
|---|---|---|
| 1 | Charge SF-1 HCl (2 g), EtOAc (60 mL). | Sample from 1779-58-5 |
| 2 | Charge 30 mL of 10% $K_2CO_3$ aqueous solution to the reactor with stirring. Continue to stir the mixture for 30 min to 1 hour. | |
| 3 | Separate the layers. Keep the organic layer in the reactor. | |
| 4 | Charge 2 g of $MgSO_4$ and 1 g of charcoal and silica gel (10 g) to the reactor. | |
| 5 | Charge dichloromethane (40 mL) to the reactor. | |
| 6 | Heat the mixture to 50° C. for 30 min. | |
| 7 | Cool the mixture to 15-25° C. | |
| 8 | Filter through Celite (5 g). Wash the cake with 50 mL of mixture EtOAc/DCM (3:2). | |
| 9 | Distill the solvent to 5-7.5 mL. Add heptane (25-32.5 mL) to the reactor. | |
| 10 | Cool the mixture to 15-25° C. Stir the mixture for 2-3 hours. | |
| 11 | Filter the precipitate formed. Wash the cake with heptane (20 mL). | |
| 12 | Dry the cake under vacuum to give 1.29 g of gray solid, yield 74%, purity 98.3%. | |

Figure 4:
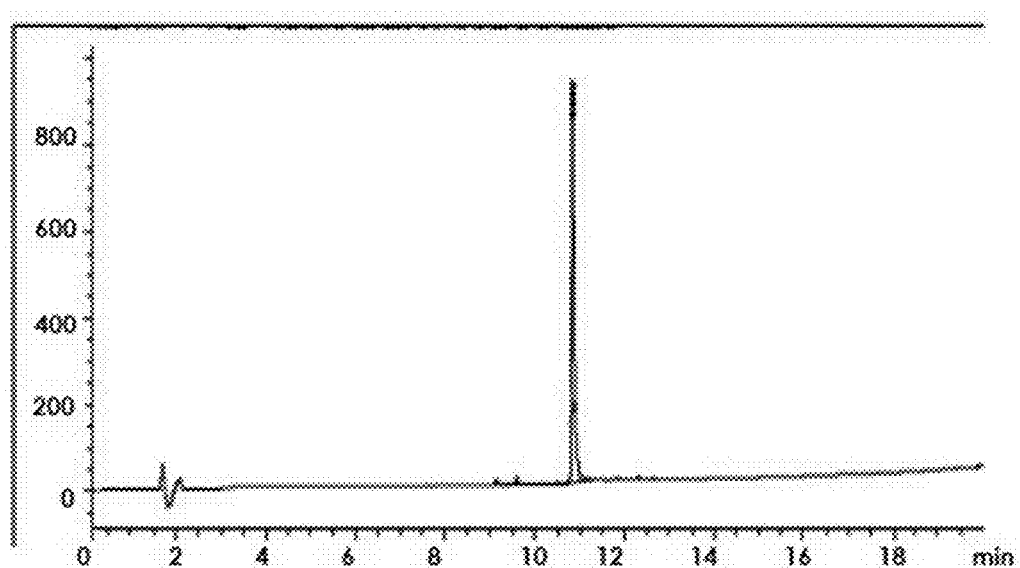
FIG. 4 is a graph depicting Decolorization of SF-1 free base

As procedure C was found to be the most effective, it was scaled up for further study. Purity was determined by HPLC (FIG. 4).

Modified Procedure C (10 g Scale)

| Op# | Operation | Note |
|---|---|---|
| 1 | Charge SF-1 HCl (10 g), EtOAc (300 mL). | Sample from 1779-58-5 |
| 2 | Charge 150 mL of 10% $K_2CO_3$ aqueous solution to the reactor with stirring. Continue to stir the mixture for 1 to 2 hours. | |
| 3 | Separate the layers. Save the organic layer. | |
| 4 | Charge 5 g of $K_2CO_3$ to the aqueous layer. Charge dichloromethane (200 mL) to the reactor. Stir the mixture for 15 to 30 minutes. Separate the layers, and charge the organic layers to the reactor. | |
| 5 | Charge 10 g of $MgSO_4$ and 5 g of charcoal and silica gel (25 g) to the combined organic layers in the reactor. | |
| 6 | Heat the mixture to 40° C. for 30 min. | |
| 7 | Cool the mixture to 15-25° C. | |
| 8 | Filter through Celite (20 g). Wash the cake with 500 mL of mixture EtOAc/DCM (3:2). | |
| 9 | Distill the solvent to 25-37.5 mL. Add heptane (125-162.5 mL) to the reactor. | |
| 10 | Cool the mixture to 15-25° C. Stir the mixture for 2-3 hours. | |
| 11 | Filter the precipitate formed. Wash the cake with heptane (100 mL). HPLC: 1779-69-11L | |
| 12 | Dry the cake under vacuum to give 7.1 g of gray solid, yield 81%, purity 98.7%. HPLC: 1779-69-12S | |

Example 3

Recrystallization from 1,4-dioxane

Procedure 1. Ratio of 1:2 (w/v) SF-1 free base to 1,4-dioxane
 1. Charge SF-1 free base (1 g, 1779-76-17) and 1,4-dioxane (2 mL).
 2. Heat the mixture to 80° C. to give a clear solution.
 3. Cool the mixture to 15-25° C. and stir at this temperature for 2-3 hours.
 4. Filter the precipitate formed.
 5. Dry the compound to give a yellow solid (0.98 g, 98%). Purity. 98.32 A %.

Procedure 2 Ratio of 1:3 (w/v) SF-1 free base to 1,4-dioxane
 1 Charge SF-1 free base (2 g, 1779-76-17) and 1,4-dioxane (6 mL).
 2. Heat the mixture to 80° C. to give a clear solution.
 3. Cool the mixture to 15-25° C. and stir at this temperature for 2-3 hours.
 4. Filter the precipitate formed. Wash the cake with 1,4-dioxane (6 mL).
 5. Dry the compound to give an off-white solid (1.94 g, 97%). Purity, 99.12 A %.

Procedure 3. Ratio of 1:5 (w/v) SF-1 free base to 1,4-dioxane
 1. Charge SF-1 free base (2 g, 1779-76-17) and 1,4-dioxane (10 mL).
 2. Heat the mixture to 80° C. to give a clear solution.
 3 Cool the mixture to 15-25° C. and stir at this temperature for 2-3 hours.
 4. Filter the precipitate formed. Wash the cake with 1,4-dioxane (10 mL).
 5. Dry the compound to give an off-white solid (1.86 g. 93%). Purity. 99.47 A %

Procedure 4. Ratio of 1:8 (w/v) SF-1 free base to 1,4-dioxane
 1. Charge SF-1 free base (1 g, 1779-76-17) and 1,4-dioxane (8 mL).
 2. Heat the mixture to 80° C. to give a clear solution.
 3. Cool the mixture to 15-25° C. and stir at this temperature for 2-3 hours.
 4. Filter the precipitate formed. Wash the cake with 1,4-dioxane (10 mL).
 5. Dry the compound to give a white solid (0.89 g, 89%). Purity. 99.76 A %.

Procedure 5. Ratio of 1:10 (w/v) SF-1 free base to 1,4-dioxane
1. Charge SF-1 free base (1 g, 1779-76-17) and 1,4-dioxane (10 mL).
2. Heat the mixture to 80° C. to give a clear solution.
3. Cool the mixture to 15-25° C. and stir at this temperature for 2-3 hours.
4. Filter the precipitate formed. Wash the cake with 1,4-dioxane (10 mL).
5. Dry the compound to give a white solid (0.87 g, 87%). Purity. 99.76 A %.

Example 4

Preparation of Hydrochloride Salt

Figure 5:
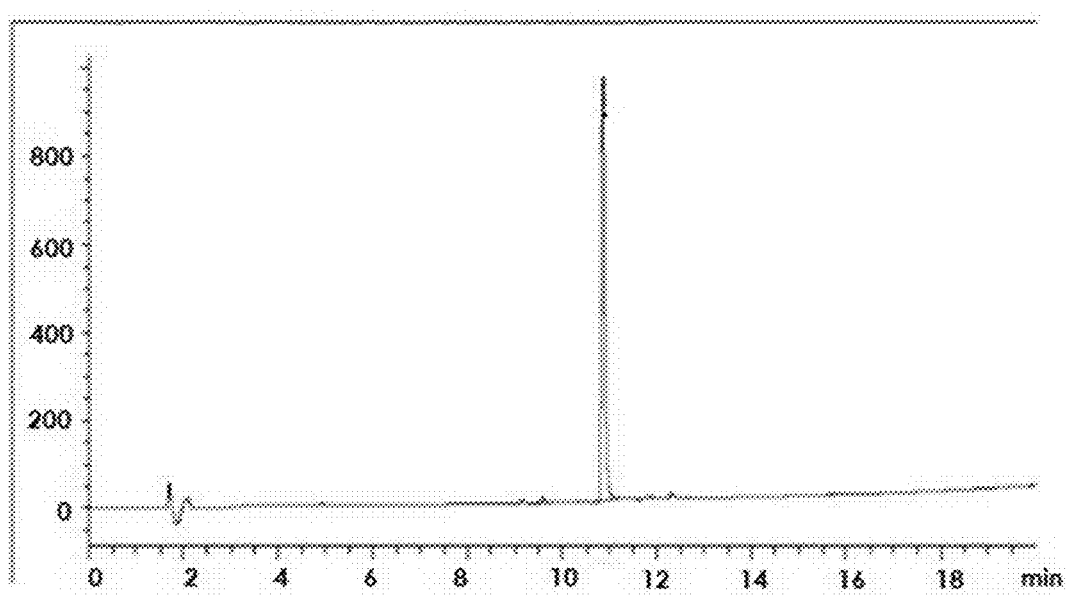
FIG. 5 is a graphs depicting the SF-1 HCl salt product was obtained in 84.8% yield and 99.5 A % purity as determined by HPLC

A 20 gm scale synthesis was conduct by acidification of SF-1 free base dissolved in ethanol with HCl dissolved in isopropanol, followed by precipitation with heptane. The SF-1 HCl salt product was obtained in 84.8% yield and 99.5 A % purity as determined by HPLC (FIG. 5).

| OP step# | Material Name | Lot# | MW | equiv | mmol | W (g) | V (mL) |
|---|---|---|---|---|---|---|---|
| 1 | SF-1 free base | 1779-97-205 | 501.5 | 1 | 39.88 | 20.00 | |
| 1 | HCl in IPA | | | 1.0 | 39.88 | | |
| 1 | EtOH | | | | | | 290 |
| 3 | Heptane | | | | | | 600 |
| 5 | EtOH | | | | | | 40 |
| 5 | Heptane | | | | | | 160 |

Procedure

| Op# | Operation | Note |
|---|---|---|
| 1 | Charge EtOH (290 mL) and HCl in IPA (3.4N, 11.8 mL, 1 eq). | |
| 2 | Charge SF-1 free base (20 g, 40 mmol). | |
| 3 | Heat the mixture to gentle reflux to give a clear solution. Stir the mixture for 15-30 min at this point. Charge heptane (600 mL) with stirring. | |
| 4 | Cool down to 15-25° C. Stir the mixture for 2-3 hours. | |
| 5 | Filter the precipitate formed. Wash the cake with EtOH-heptane (1:4, 200 mL). | |
| 6 | Dry the compound. 18.2 g (84.8% yield) 99.5 A % | |
| 7 | Check XRPD (1779-106-6S) | |

Example 5

Synthesis of SF-Int2A

SF-Int2A was synthesized on a 200 g scale. The materials used are listed below. The product was obtained in 91% yield with 99 A % purity.

| OP # | Material Name | MW | eq | mmol | W (g) | V (mL) |
|---|---|---|---|---|---|---|
| 1 | SM-1 | 307.44 | 1 | 0.65 | 200.00 | |
| 1 | SM-2A | 150.18 | 1 | 0.65 | 97.70 | |
| 1 | Cs$_2$CO$_3$ | 325.82 | 1 | 0.65 | 211.96 | |
| 1 | 1,4-dioxane | 88.11 | | | | 1200 |
| 2 | Pd$_2$(dba)$_3$ | 915.7 | 0.005 | 0.003253 | 2.98 | |
| 2 | Xantphos | 578.63 | 0.015 | 0.0098 | 5.65 | |
| 5 | Celite | | | | 50.00 | |
| 5 | EtOAc | | | | | 2400 |
| 6, 6 | 10% NaCl | | | | | 1200 |
| 7, 7 | 7% NaHCO$_3$ | | | | | 1200 |
| 8 | 10% NaCl | | | | | 600 |
| 10 | Heptane | | | | | 3000 |
| 12 | Heptane | | | | | 600 |

Procedure

| Op# | Operation |
|---|---|
| 1 | Charge 200 g (0.65 mol) of SM-1, 97.7 g (0.65 mmol) of SM-2A, 211.96 g (0.65 mmol) of Cs$_2$CO$_3$, and 1,4-dioxane (1200 mL). |
| 2 | Charge Pd$_2$(dba)$_3$ (2.98 g) and Xantphos (5.65 g). |
| 3 | Heat the mixture for 2-3 days. |
| 4 | Monitor the reaction with HPLC. After 45 hours, there was 0.52% of SM-1 left. |
| 5 | Cool the mixture down to room temperature. Filter through a pad of Celite (50 g). Wash the cake with EtOAc (2400 mL). |
| 6 | Wash the organic layer with 10% NaCl (2 × 600 mL). |
| 7 | Wash the organic layer with 7% NaHCO$_3$ (2 × 600 mL). |
| 8 | Wash the organic layer with 10% NaCl (600 mL). |
| 9 | Distill the solvent to around a volume of 350-400 mL left. |
| 10 | Charge 3000 mL of heptane with stirring. |
| 11 | Cool down to room temperature and stir the mixture overnight. |
| 12 | Filter the precipitate formed and wash the cake with heptane (650 mL). |
| 13 | Dry the compound under vacuum to give 195 g, yield 91%. Purity 99% |

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:
1. A method of synthesizing a compound of formula (I)

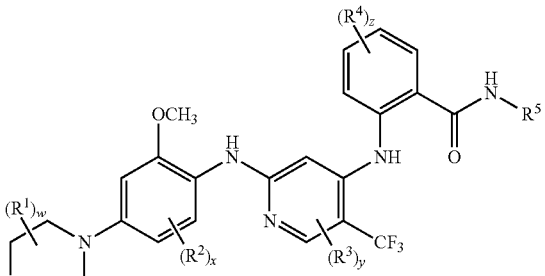

wherein
R$^1$ is independently at each occurrence alkyl, aryl, cycloalkyl, heterocyclyl, aryl, or heteroaryl;

R², R³ and R⁴ are independently at each occurrence alkyl, aryl, cycloalkyl, heterocyclyl, aryl, heteroaryl, alkoxy, aryloxy, or fluoro;
R⁵ is hydrogen, alkyl, aryl, cycloalkyl, heterocyclyl, aryl, or heteroaryl;
w is 0 to 8;
x is 0 to 3;
y is 0 to 2; and
z is 0 to 4;
including any stereoisomer thereof;
comprising contacting a compound of formula (II)

Formula (II)

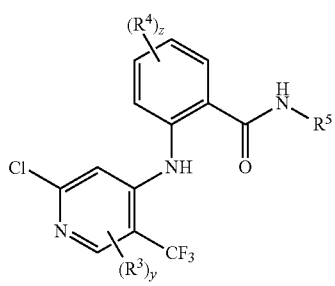

and a compound of formula (III)

Formula (III)

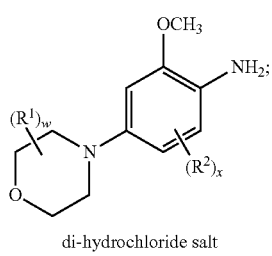

di-hydrochloride salt under conditions comprising:
(a) a solution of compounds (II) and (III) in a liquid hydroxylic solvent of boiling point higher than about 115 degrees C.;
(b) the compound of formula (II) being present at a concentration of no less than about 0.4 M;
(c) the compound of formula (III) being present at a concentration about 10% higher than the concentration of the compound of formula (II);
(d) a temperature in excess of about 100° C.;
(e) a duration of time of at least about 48 hours;
(f) an absence of added bases;
(g) an absence of transition metal catalysts;
followed by precipitation of the compound of formula (I) by addition of a hydrocarbon to the hydroxylic solvent following cooling of the solvent to ambient temperature, then collection of the precipitated compound.

2. The method of claim 1 wherein the hydroxylic solvent is n-butanol, methoxyethanol, or ethoxyethanol.

3. The method of claim 1 wherein the concentration of the compound of formula (II) is about 0.5 M.

4. The method of claim 1 wherein the temperature is about 118-166° C.

5. The method of claim 1 wherein the hydrocarbon is heptane.

6. The method of claim 1 wherein the yield of the compound of formula (I) is at least about 75%.

7. The method of claim 1 wherein the purity of the compound of formula (I) is at least about 98%.

8. The method of claim 1 wherein the compound of formula (I) is a compound of formula

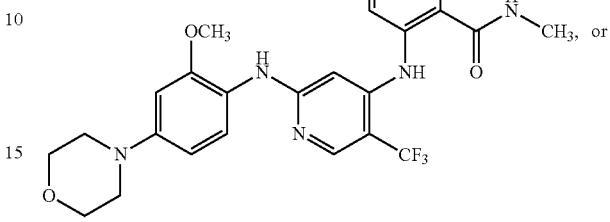

or

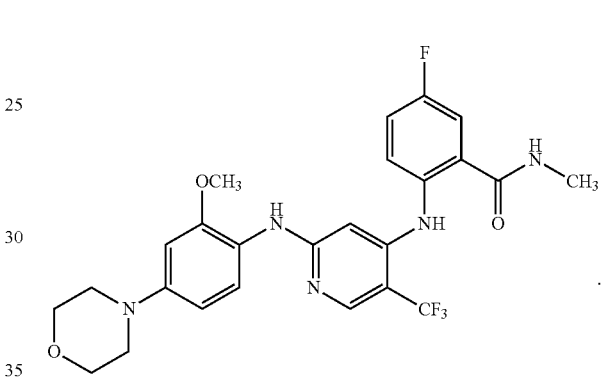

9. The method of claim 1 wherein the compound of formula (II) is a compound of formula

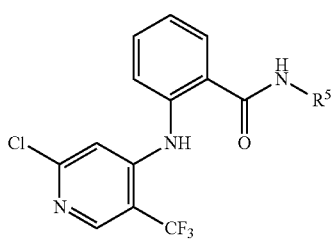

wherein R⁵ is methyl,
or a compound of formula

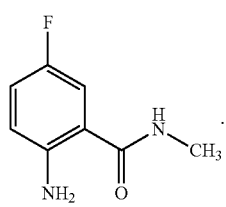

10. The method of claim 1 wherein the compound of formula (III) is a compound of formula

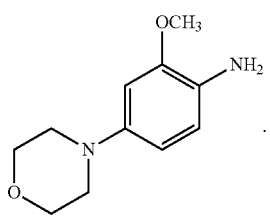 [SMILES: COc1cc(N2CCOCC2)ccc1N]

11. The method of claim 1, further comprising purification of the compound of formula (I), comprising:
(a) first, dissolving and partitioning the compound of formula (I) between aqueous base and a water-immiscible organic solvent, then separating a solution of the compound of formula (I) free base in the water-immiscible organic solvent;
(b) then, adding to the solution silica gel, and optionally anhydrous magnesium sulfate, and optionally activated charcoal, then separating the solid material from the solvent to provide a purified solution of free base;
(c) then, adding a hydrocarbon to the purified solution to cause precipitation of the free base; and
(d) then, collecting the precipitated free base of the compound of formula (I).

12. The method of claim 11 wherein the aqueous base comprises aqueous carbonate.

13. The method of claim 12 wherein the carbonate is potassium carbonate.

14. The method of claim 11 wherein the water immiscible solvent is ethyl acetate, dichloromethane, or any mixture thereof.

15. The method of claim 11 wherein separating the solid material comprises filtration or centrifugation, or both.

16. The method of claim 11 wherein the hydrocarbon is heptane.

17. The method of claim 11 wherein collecting the free base comprises filtration or centrifugation, or both.

18. The method of claim 11 wherein the free base is a compound of formula

19. The method of claim 11 wherein the yield of the compound of formula (I) is at least about 70%.

20. The method of claim 11 wherein the purity of the compound of formula (I) is at least about 98%.

21. The method of claim 11 further comprising converting the free base of the compound of formula (I) to a hydrochloride salt thereof by a process comprising:
(a) contacting a first alcoholic solution of the free base and a second alcoholic solution of hydrogen chloride, then
(b) adding a hydrocarbon to precipitate the compound of formula (I) hydrochloride salt; then
(c) collecting the compound of formula (I) hydrochloride salt.

22. The method of claim 21 wherein the first alcoholic solution is in ethanol.

23. The method of claim 21 wherein the second alcoholic solution is in isopropanol.

24. The method of claim 21 wherein the hydrocarbon is heptane.

25. The method of claim 21 wherein the hydrochloride salt of the compound of formula (I) is a mono-hydrochloride salt.

26. The method of claim 21 further comprising, after collecting the compound of formula (I) hydrochloride salt, then recrystallizing the compound from 1,4-dioxane.

27. The method of claim 26 wherein the compound of formula (I) hydrochloride salt is of at least 99% purity.

28. The method of claim 26 wherein a recrystallization yield is at least about 85%.

29. The method of claim 21 wherein the yield of formula (I) hydrochloride salt is at least about 70%.

30. The method of claim 21 wherein the purity of the formula (I) hydrochloride salt is at least about 97%.

31. The method of claim 26 wherein a compound of formula

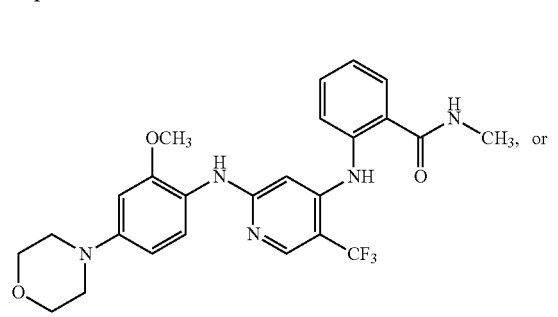

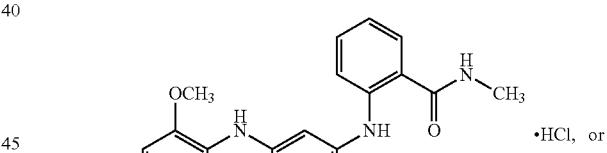

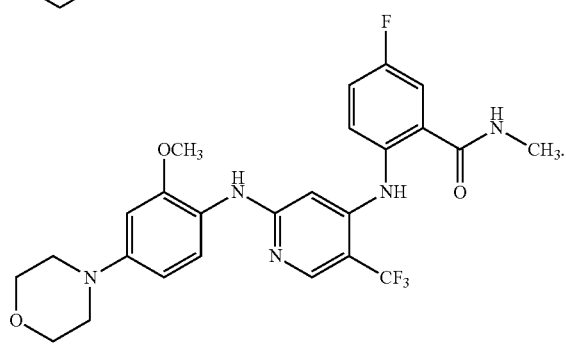

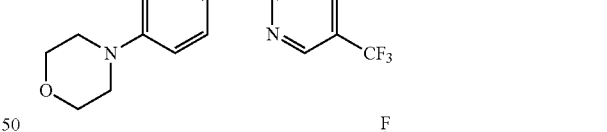

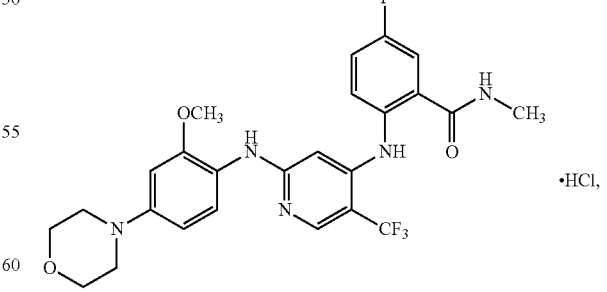

is obtained in at least about 60% overall yield and at least about 99% purity.

* * * * *